United States Patent
Lee et al.

(10) Patent No.: US 6,541,618 B1
(45) Date of Patent: Apr. 1, 2003

(54) NITRO-SUBSTITUTED NON-FLUORESCENT ASYMMETRIC CYANINE DYE COMPOUNDS

(75) Inventors: Linda G. Lee, Palo Alto, CA (US); Ronald J. Graham, Pleasanton, CA (US); Khairuzzaman B. Mullah, Union City, CA (US); Francis T. Haxo, San Francisco, CA (US)

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 09/602,544

(22) Filed: Jun. 21, 2000

Related U.S. Application Data (62) Division of application No. 09/012,525, filed on Jan. 23, 1998, now Pat. No. 6,080,868.

(51) Int. Cl.[7] ............ C07H 21/02; C07H 19/04; C07D 293/00; C07D 421/00; C07D 293/10

(52) U.S. Cl. ............ 536/23.1; 536/25.3; 536/26.6; 548/100; 548/120; 548/146; 548/148; 548/181; 548/215; 548/217; 548/223

(58) Field of Search ............ 548/100, 120, 548/146, 148, 181, 215, 217, 223; 536/23.1, 25.3, 26.6

(56) References Cited

U.S. PATENT DOCUMENTS

| | | | |
|---|---|---|---|
| 4,883,867 A | 11/1989 | Lee et al. | 536/28 |
| 5,321,130 A | 6/1994 | Yue et al. | 536/23.1 |
| 5,410,030 A | 4/1995 | Yue et al. | 536/23.1 |
| 5,436,134 A | 7/1995 | Haugland et al. | 435/34 |
| 5,534,416 A | 7/1996 | Millard et al. | 436/34 |
| 5,582,977 A | 12/1996 | Yue et al. | 435/6 |
| 5,656,449 A | 8/1997 | Yue | 435/34 |
| 5,658,735 A | 8/1997 | Lee | 435/6 |
| 5,658,751 A | 8/1997 | Yue et al. | 435/34 |
| 5,863,753 A | 1/1999 | Haugland et al. | 435/34 |

FOREIGN PATENT DOCUMENTS

| | | |
|---|---|---|
| EP | 0 710 668 | 5/1996 |
| EP | WO 96/15270 | 5/1996 |
| EP | 0 714 986 | 6/1996 |
| JP | 09 288326 | 11/1997 |
| WO | WO 96/04405 | 2/1996 |
| WO | WO 97/45539 | 12/1997 |

OTHER PUBLICATIONS

Benson et al., "Fluorescence Energy–Transfer Cyanine Heterodimers with High Affinity for Double–Stranded DNA," *Analytical Biochemistry*, 231:247–255 (1995).

(List continued on next page.)

*Primary Examiner*—Jezia Riley
(74) *Attorney, Agent, or Firm*—Alex Andrus; Paul D. Grossman

(57) ABSTRACT

The invention provides an asymmetric cyanine dye compound having the structure

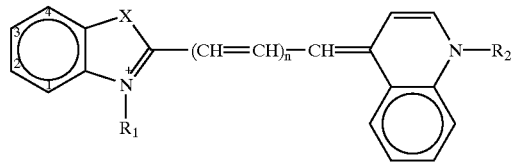

including substituted forms thereof, wherein, at least one of $R_1$ and $R_2$ is linking group, X is O, S, or Se, and n ranges from 0 to 2. The invention further provides reporter-quencher dye pairs comprising the asymmetric cyanine dyes, dye-labelled polynucleotides incorporating the asymmetric cyanine dyes, and hybridization detection methods utilizing the dye-labelled polynucleotides.

20 Claims, 8 Drawing Sheets

OTHER PUBLICATIONS

Brooker et al., "Color and Constitution. V. The Absorption of Unsymmetrical Cyanines Resonance as a basis for a Classification of Dyes," *JACS* 64:199–210 (Feb. 1942).

Ficken, G.E., "Cyanine Dyes," *The Chemistry of Synthetic Dyes*, vol. IV, Vewkataraman, Chapt. V. pp. 211–340 (1971).

Hung et al., "Cyanine Dyes with High Absorption Cross Section as Donor Chromophores in Energy Transfer Primers," *Analytical Biochemistry* 243:15–27 (1996).

Inagaki et al., "Photothermographic material," *Chemical Abstracts* 218(4):1162 (Jan. 26, 1998).

Lee et al., "Thiazole Orange: A New Dye for Reticulocyte Analysis," *Cytometry* 7:508–517 (1986).

Mujumdar et al., "Cyanine Dye Labeling Reagents: Sulfoindocyanine Succinimidyl Esters," *Bioconjucate Chem.* 4(2):105–111 (1993).

1) 8, iPr$_2$NEt, CH$_3$OH
2) HCl

NITRO-SUBSTITUTED NON-FLUORESCENT ASYMMETRIC CYANINE DYE COMPOUNDS

This application is a division of application Ser. No. 09/012,525, filed on Jan. 23, 1998, now U.S. Pat. No. 6,080,868, which is incorporated herein by reference.

FIELD OF THE INVENTION

This invention relates to dye compounds useful as quenchers in a reporter-quencher energy-transfer dye pair. More specifically, this invention relates to cyanine quencher compounds, reagents incorporating such compounds and methods utilizing such compounds and/or reagents.

BACKGROUND

Nucleic acid hybridization assays comprise an important class of techniques in modem biology. Such assays have diverse applications including the diagnosis of inherited disease, human identification, identification of microorganisms, paternity testing, virology, and DNA sequencing, i.e., sequencing by hybridization.

An important aspect of nucleic acid hybridization assays is the method used to facilitate detection of the hybridization event. A particularly important class of methods used in nucleic acid hybridization assays employs a reporter-quencher energy-transfer dye pair comprising a "reporter" dye and a "quencher" dye which interact through a fluorescence resonance energy transfer (FRET) process. In these methods, the reporter is a luminescent compound that can be excited either by chemical reaction, producing chemiluminescence, or by light absorption, producing fluorescence. The quencher can interact with the reporter to alter its light emission, usually resulting in the decreased emission efficiency of the reporter. This phenomenon is called quenching. The efficiency of quenching is a strong function of the distance between the reporter molecule and the quencher molecule. Thus, in a nucleic acid hybridization assay, detection of a hybridization event is accomplished by designing an energy transfer system in which the spacing between a reporter and a quencher is modulated as a result of the hybridization.

Quenchers which are presently used in FRET-based nucleic acid hybridization assays are themselves fluorescent. That is, in addition to quenching the fluorescence of the reporter, the quencher produces fluorescent emissions. This is problematic, particularly in assays employing multiple spectrally-resolvable reporters, because the quencher fluorescence can interfere with the fluorescent signal produced by one or more of the reporters.

Thus, there remains a continuing need for quencher dyes which are themselves substantially non-fluorescent.

SUMMARY

The present invention is directed towards our discovery of a class of non-fluorescent cyanine quencher compounds which are useful in the context of a reporter-quencher energy-transfer dye pair. These quencher compounds find particular application in nucleic acid hybridization assays employing fluorescence energy transfer as a means of detection.

In a first aspect, the invention comprises an asymmetric cyanine dye compound having the structure including substituted forms thereof, wherein at least one of $R_1$ and $R_2$ is linking group, X is O, S, or Se, and n ranges from 0 to 2.

In a second aspect, the invention includes a reporter-quencher energy-transfer dye pair comprising a reporter dye and a quencher dye, wherein the quencher dye is an asymmetric cyanine dye compound of the first aspect.

In a third aspect, the invention includes a an oligonucleotide having a cyanine dye quencher according to the first aspect covalently attached thereto.

In a fourth aspect, the invention provides a method for detecting a target nucleic acid sequence including the steps of providing a sample nucleic acid including at least one target nucleic acid sequence, and hybridizing a labelled oligonucleotide probe to the target nucleic acid sequence, the labelled oligonucleotide probe being labelled with an asymmetric cyanine dye compound of the first aspect. In a particularly preferred embodiment of this fourth aspect, the method further includes the step of digesting the oligonucleotide probe such that one or both of the reporter and quencher dyes is removed from the oligonucleotide probe.

Various aspects and embodiments of the above-described invention achieve one or more of the following important advantages over known quencher dye compounds. The asymmetric cyanine quenchers of the present invention may be easily covalently linked to a reagent, e.g., a polynucleotide. Furthermore, oligonucleotide probes labelled with the asymmetric cyanine quenchers of the present invention exhibit enhanced hybridization stability as compared to conventionally labelled probes, thereby allowing for the use of shorter probes which are more sensitive to hybridization mismatches. In addition, the asymmetric cyanine quenchers of the present invention are essentially non-fluorescent, thereby providing additional spectrum which can be occupied by one or more additional reporters.

These and other objects, features, and advantages of the present invention will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. DEFINITIONS

Unless stated otherwise, the following terms and phrases as used herein are intended to have the following meanings:

"Energy transfer" and "fluorescence quenching" refer to a processes whereby energy is removed from an electronically excited luminescent "reporter" molecule by a "quencher" molecule, thereby returning the reporter molecule to its ground state without the emission of light from the reporter molecule. The reporter molecule may be excited to one of its higher energy levels by any of a number of process, including light absorption and chemical reaction.

"Spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of a fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, New York, 1985).

"Linking group" means a moiety capable of reacting with a "complementary functionality" attached to a reagent, such reaction forming a "linkage" connecting a dye to a reagent. Preferred linking groups include isothiocyanate, sulfonyl chloride, 4,6-dichlorotriazinyl, carboxylate, succinimidyl ester, or other active carboxylate whenever the complementary functionality is amine. Alternatively, the linking group may be amine. Preferably the linking group is maleimide, halo acetyl, or iodoacetamide whenever the complementary finctionality is sulfhydryl. See R. Haugland, *Molecular Probes Handbook of Fluorescent Probes and Research Chemicals*, Molecular probes, Inc. (1992). In a particularly preferred embodiment, the linking group is a N-hydroxysuccinimidyl (NHS) ester and the complementary functionality is an amine, where to form the NHS ester, a dye of the invention including a carboxylate linking group is reacted with dicyclohexylcarbodiimide and N-hydroxysuccinimide.

"Lower alkyl" denotes straight-chain and branched hydrocarbon moieties containing from 1 to 8 carbon atoms, e.g., methyl, ethyl, propyl, isopropyl, tert-butyl, isobutyl, sec-butyl, neopentyl, tert-pentyl, and the like.

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position. When the nucleoside base is purine or 7-deazapurine, the sugar moiety is attached at the 9-position of the purine or deazapurine, and when the nucleoside base is pyrimidine, the sugar moiety is attached at the 1-position of the pyrimidine, e.g., Kornberg and Baker, *DNA Replication*, 2nd Ed. (Freeman, San Francisco, 1992). The term "nucleotide" as used herein refers to a phosphate ester of a nucleoside, e.g., triphosphate esters, wherein the most common site of esterification is the hydroxyl group attached to the C-5 position of the pentose. The term "nucleoside/tide" as used herein refers to a set of compounds including both nucleosides and nucleotides. "Analogs" in reference to nucleosides/tides include synthetic analogs having modified base moieties, modified sugar moieties and/or modified phosphate moieties, e.g. described generally by Scheit, *Nucleotide Analogs* (John Wiley, New York, 1980). Phosphate analogs comprise analogs of phosphate wherein the phosphorous atom is in the $^+5$ oxidation state and one or more of the oxygen atoms is replaced with a non-oxygen moiety. Exemplary phosphate analogs include but are not limited to phosphorothioate, phosphorodithioate, phosphoroselenoate, phosphorodiselenoate, phosphoroanilothioate, phosphoranilidate, phosphorarnidate, boronophosphates, including associated counterions, e.g., $H^+$, $NH_4^+$, $Na^+$, if such counterions are present. Exemplary base analogs include but are not limited to 2,6-diaminopurine, hypoxanthine, pseudouridine, C-5-propyne, isocytosine, isoguanine, 2-thiopyrimidine, and other like analogs. Exemplary sugar analogs include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, amino or alkylamino, fluoro, chloro and bromo. The term "labelled nucleoside/tide" refers to nucleosides/tides which are covalently attached to a label.

"Polynucleotide" or "oligonucleotide" means polymers of natural nucleotide monomers or analogs thereof, including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, if such counterions are present. Polynucleotides typically range in size from a few monomeric units, e.g. 5–40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes deoxythymidine, unless otherwise noted.

"Substituted" as used herein refers to a molecule wherein one or more hydrogen atoms are replaced with one or more non-hydrogen atoms, functional groups or moieties. For example, an unsubstituted nitrogen is —NH$_2$, while a substituted nitrogen is —NHCH$_3$. Exemplary substituents include but are not limited to halo, e.g., fluorine and chlorine, lower alkyl, lower alkene, lower alkyne, sulfate, sulfonate, sulfone, amino, ammonium, amido, nitrile, lower alkoxy, phenoxy, aromatic, phenyl, polycyclic aromatic, electron-rich heterocycle, and linking group.

"Methine bridge" or "polymethine bridge" refers to a portion of a cyanine dye compound connecting two base portions, the bridge having the following structure where n typically ranges from 0 to 2.

"Xanthene dyes" are dyes which comprise the following fused three-ring structure where R is oxygen (fluorescein) or —NH (rhodamines), including substituted forms thereof. Exemplary substituted fluorescein compounds include the "NED" dye which has the structure the "TET" dye which has the structure and the "FAM" dye which has the structure

An exemplary rhodamine dye is the "TAMRA" or "TMR" dye which has the structure

"Coumarin dyes" are dyes which comprise the following fused two-ring structure where R is oxygen (hydroxycoumarin) or —NH (aminocoumarin), including substituted forms thereof.

"BODIPY™ dyes" are dyes comprising the following fused ring structure including substituted forms thereof. See the *Handbook of Fluorescent Probes and Research Chemicals, Sixth Addition*, Haugland, Molecular Probes, Inc. (1996).

"Cyanine dyes" are dyes comprising two nitrogen-heterocyclic rings joined by a methine, or polymethine, bridge. An exhaustive review of such dyes is provided by Ficken (Ficken, *The Chemistry of Synthetic Dyes*, Vol IV, Venkataraman (1971)).

I. ASYMMETRIC CYANINE DYE COMPOUNDS

A. Structure

In a first aspect, the present invention comprises a novel class of cyanine dye compounds useful as non-fluorescent quenchers. These compounds have the general structure shown in Formula I immediately below, including substituted fonns thereof, where at least one of R$_1$ and R$_2$ is linking group, X is O, S, or Se, and n ranges from 0 to 2. (Note that all molecular structures provided herein are intended to encompass not only the exact electronic structures presented, but also include all resonant structures, protonation states and associated counterions thereof.)

FORMULA 1

Preferably, when the compound is to be used as a non-fluorescent quencher, the compound includes a nitro C-3 substituent. For example, compounds 5, 9, 20, 21 and 23.

In an alternative preferred embodiment, the linking group of the compound of Formula 1 is a lower alkylamine or a lower alkylcarboxy moiety, where a particularly preferred lower alkylcarboxy is $-(CH_2)_nN^+(CH_3)_2(CH_2)_nCO_2H$, where n ranges from 2 to 12. For example, compound 23.

In another preferred embodiment, one of $R_1$ or $R_2$ is $-CCH_2)_nN^+(CH_3)_3$, where n ranges from 2 to 12, and the other of $R_1$ or $R_2$ is linking group.

In yet another preferred embodiment, the X-group in the cyanine compounds of the invention is sulfur. For example, compounds 5, 9, 20, 21, 22 and 23.

In another preferred embodiment, the compound of Formula 1 includes a fused aromatic, or substituted aromatic, substituent bonded at positions 1 and 2, positions 2 and and/or positions 3 and 4. More preferably, the substituted aromatic includes one or more nitro substituents. For example, compounds 21 and 22.

In an additional preferred embodiment of the present invention, the compound of Formula 1 includes a bridging group that when taken together with $R_1$ and the proximate carbon of the methine bridge forms a ring structure having 5 to 7 members, more preferably 6 members. For example, compounds 20 and 21.

B. Synthesis

Generally, the non-fluorescent cyanine dye quenchers may be prepared as follows. See FIGS. 2A and 2B. A quaternized benzazole derivative, e.g. a benzothiazolium salt 10 or 13, is mixed with a lepidinium salt, 11, and refluxed under basic conditions, e.g. diisopropylethylamine in methanol, or pyridine. The solvent is evaporated and the crude solid is washed with dilute hydrochloric acid, e.g., 5% in water, and dried.

Figure 1A:
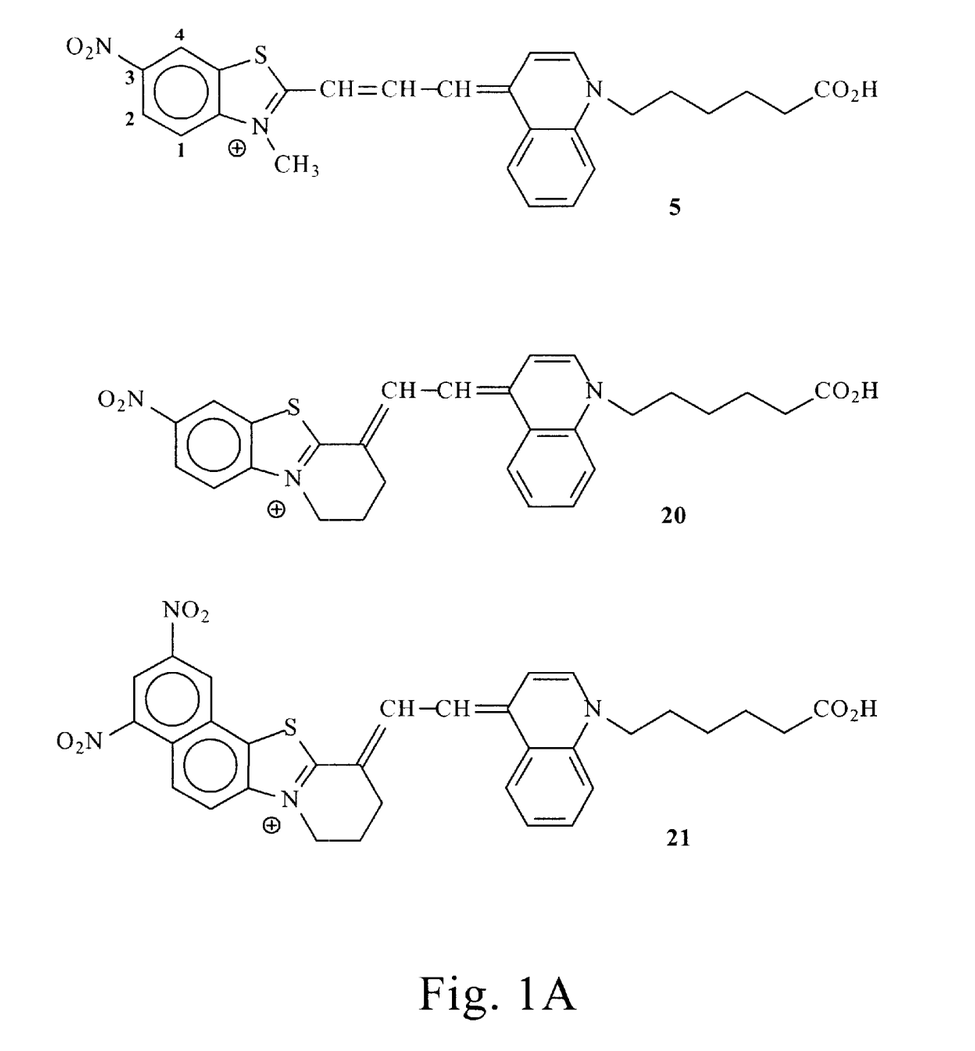
FIGS. 1A and 1B show several preferred cyanine dye compounds of the present invention.
Figure 1B:
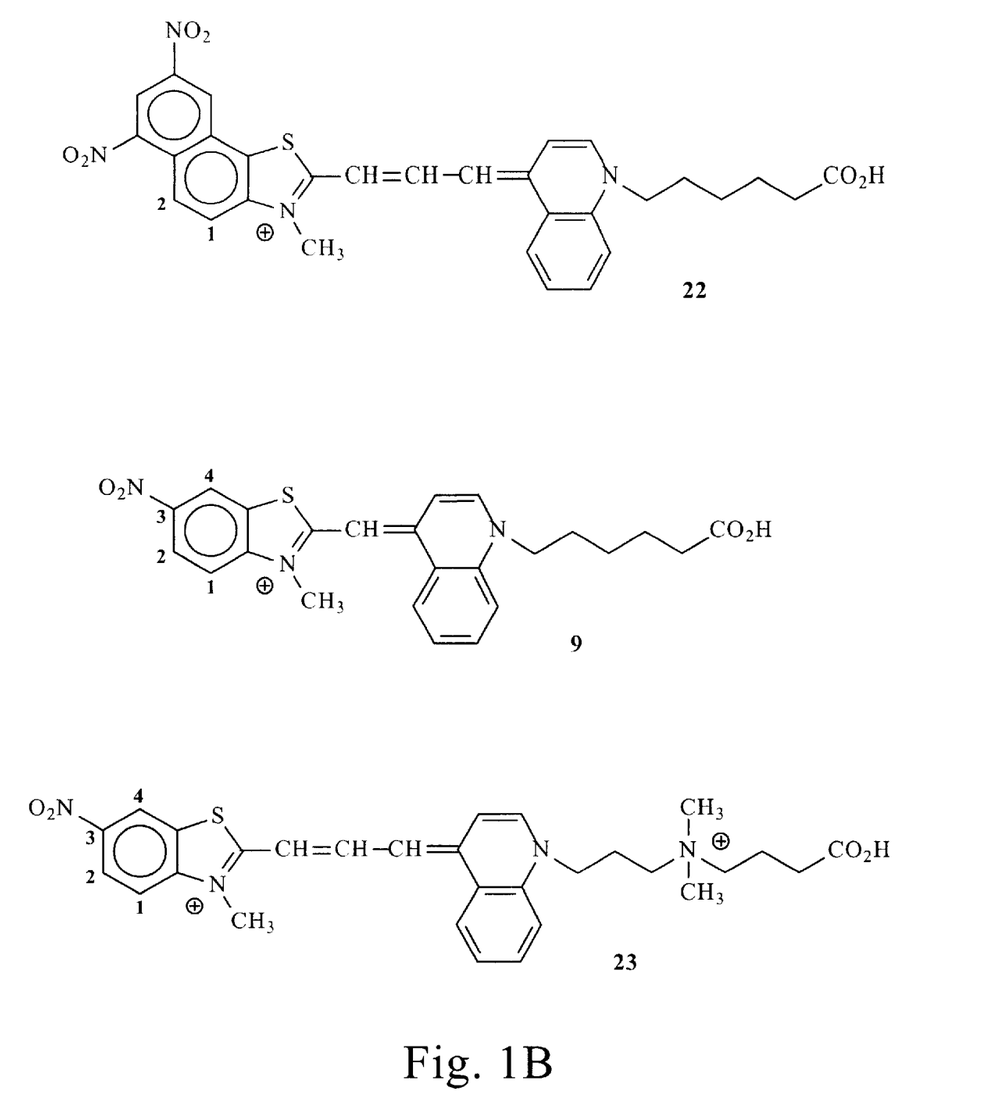
Figure 2A:
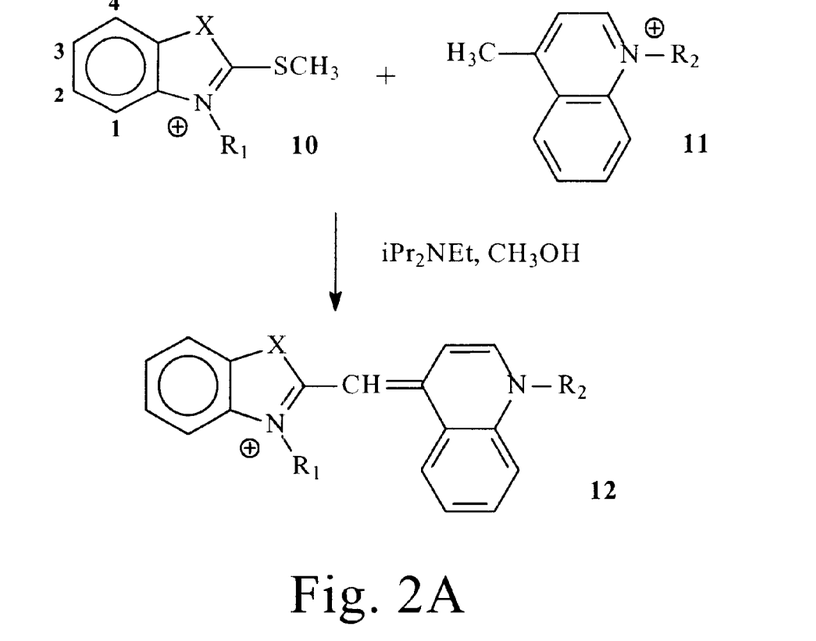
FIGS. 2A and 2B show a generalized synthetic scheme for the synthesis of the cyanine dye quenchers of the present invention.
Figure 2B:
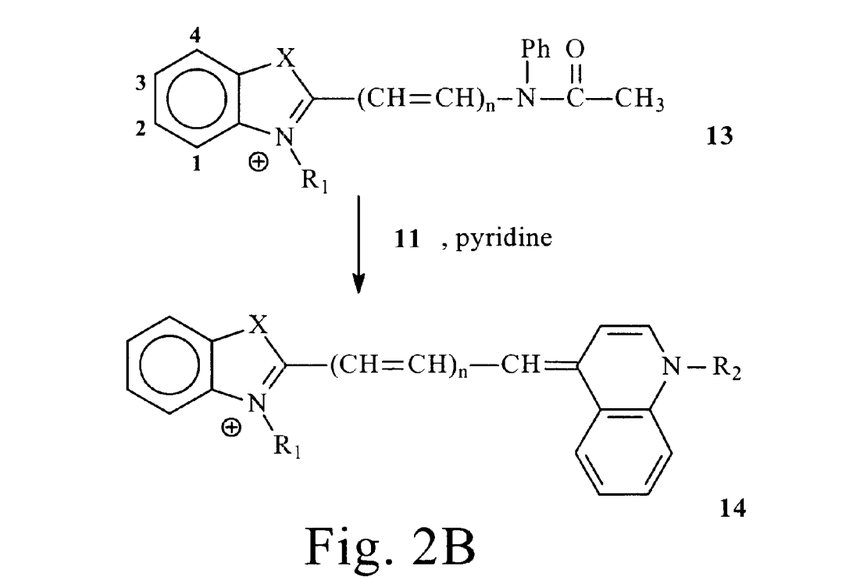

The dyes may be rendered amino-reactive by converting a carboxylic acid group to a succinimidyl ester. For example, dye 12 or 14 is dissolved in DMF with succinimidyl tetramethyluronium salt and DIPEA. The product is precipitated by the addition of dilute HCl, washed and dried.

II. DYE PAIRS INCLUDING NON-FLUORESCENT CYANINE DYES

Reporter-quencher dye pairs may be composed of any pair of molecules which can participate in an energy transfer process. Exemplary reporters may be selected from xanthene dyes, including fluoresceins, and rhodamine dyes. Many suitable forms of these compounds are commercially available with various substituents on their xanthene rings which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include but are not limited to 3-phenyl-7-isocyanatocoumarin, acridines, such as 9-isothiocyanatoacridine and acridine orange, N-(p-(2-benzoxazolyl)phenyl)maleimide, benzoxadiazoles, stilbenes, pyrenes, and the like.

Preferably, reporter molecules are selected from fluorescein and rhodamine dyes. These dyes and appropriate linking methodologies for attachment to oligonucleotides are described elsewhere (Khanna et al (cited above); Marshall, Histochemical J., 7: 299–303 (1975); Menchen et al, U.S. Pat. No. 5,188,934; Menchen et al, European Patent Application No. 87310256.0; and Bergot et al, International Application PCT/US90/05565). Particularly preferred reporter molecules include fluorescein dyes NED, TET and FAM.

Exemplary reporter-quencher pairs include the following:

| Reporter | Quencher |
|---|---|
| FAM | Nitrothiazole Orange (Compound 9) |
| FAM | Nitrothiazole Blue (Compound 5) |
| TET | Nitrothiazole Blue (Compound 5) |
| TET | Nitrothiazole Blue (Compound 5) |
| NED | Nitrothiazole Blue (Compound 5) |

III. DYE-LABELLED POLYNUCLEOTIDES

In another aspect, the present invention comprises polynucleotides labelled with the non-fluorescent cyanine dyes of the invention. Such labelled polynucleotides are useful in a number of important contexts including as oligonucleotide hybridization probes and oligonucleotide ligation probes.

Singly- or doubly-labelled polynucleotides may be prepared using any of a number of well known methods. Methods suitable for labeling an oligonucleotide at the 3' end include but are by no means limited to (1) periodate oxidation of a 3'-terminal ribonucleotide, followed by reaction with an amine-containing label (Heller and Morrison, In Rapid Detection and Identification of Infectious Agents (D. T. Kingsbury and S. Falkow, eds.), pp 245–256, Academic Press (1985)); (2) enzymatic addition of a 3'-aliphatic amine-containing nucleotide using deoxynucleotidyl transferase, followed by reaction with an amine-reactive label (Morrison, European Patent Application No. 232 967); and (3) periodate oxidation of a 3'-ribonucleotide, followed by reaction with 1,6-hexanediamine to provide a 3'-terminal aliphatic amine, followed by reaction with an amine-reactive label (Cardullo et al., Proc. Natl. Acad. Sci. USA, 85: 8790–8794 (1988)).

Methods for labeling the 5' end of an oligonucleotide include (1) periodate oxidation of a 5'-to-5'-coupled ribonucleotide, followed by reaction with an amine-reactive label (Heller and Morrison, 1985); (2) condensation of ethylenediamine with 5'-phosphorylatedpolynucleotide, followed by reaction with an amine reactive label (Morrison, 1987); and (3) introduction of an aliphatic amine substituent using an aminohexyl phosphite reagent in solid-phase DNA synthesis, followed by reaction with an amine reactive label (Cardullo, 1988).

In addition to these end-labeling methods, labels can be placed at specific locations within synthetic polynucleotides using amine-containing nucleotide phosphoramidite reagents, e.g., 5'-dimethoxytrityl-5-[N-trifluoroacetylaminohexyl)-3-acrylimido]-2-deoxyuridine, 3'-[(2-cyanoethyl)-(N,N-diisopropyl)]-phosphoramidite, e.g., Amino-Modifier C6 dT phosphoramidite (Linker Arm Nucleotide, Glen Research, Inc.) (Mathies et al., U.S. Pat. No. 5,688,648).

For a through review of oligonucleotide labeling procedures see R. Haugland in *Excited States of Biopolymers*, Steiner ed., Plenum Press (1983), *Fluorogenic Probe Design and Synthesis: A Technical Guide*, PE Applied Biosystems (1996), and G. T. Herman, *Bioconjugate Techniques*, Academic Press (1996).

Generally, the design of oligonucleotide hybridization probes including the non-fluorescent cyanine dye quenchers of the invention follows conventional teachings. Thus, in designing labelled oligonucleotide hybridization probes, the following general guidelines should be followed: (1) if the target nucleic acid sequence is located within a PCR amplicon, the probe sequence should be such that the probe hybridizes at a location on the sequence between the PCR primers; (2) probes should be about 20–30 nucleotides long so as to ensure good hybridization kinetics and specificity of binding; (3) avoid secondary structure in the probe and target nucleic acid sequence; (4) if the probe is being used in combination with a pair of PCR primers, the probe should not hybridize to either of the forward and reverse primers; and (5) avoid probes with long stretches of a single nucleotide, i.e., more than four; and (6) when choosing between a probe sequence and its complement, pick the strand that has more C nucleotides than G nucleotides.

IV. HYBRIDIZATION METHODS UTILIZING NON-FLUORESCENT CYANINE DYES

Several hybridization assay formats that employ energy transfer as a means for detecting hybridization have been described, five of which are discussed below and shown schematically in FIGS. 5A–E.

Figure 5A:
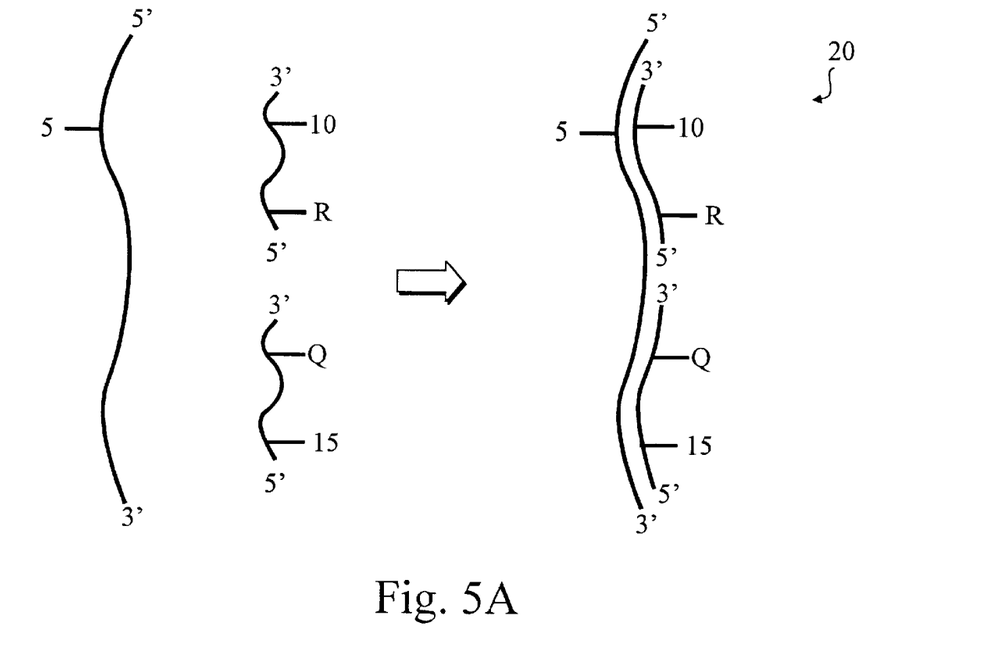
FIGS. 5A–5E shows a schematic depiction of several hybridization detection methods according to the present invention.

In a first assay format, shown in FIG. 5A, the sequences of two oligonucleotide probes are selected such that they will hybridize to contiguous regions of a target nucleic acid 5. The first probe 10, hybridizing toward the 5'-terminus of the target nucleic acid, is labelled near its 5'-terminus with a reporter label, whereas the second probe 15 is labelled near its 3'-terminus with a quencher label. Thus, when a 3-way hybrid 20 is formed among the target nucleic acid 5 and the first 10 and second 15 probes, the reporter and quencher are brought into close proximity and energy transfer can take place. Thus, in this format, the emission of the reporter is quenched upon the hybridization of the two probes to the target. (Heller et al., European Patent Application No. 070 685 (1983))

Figure 5B:
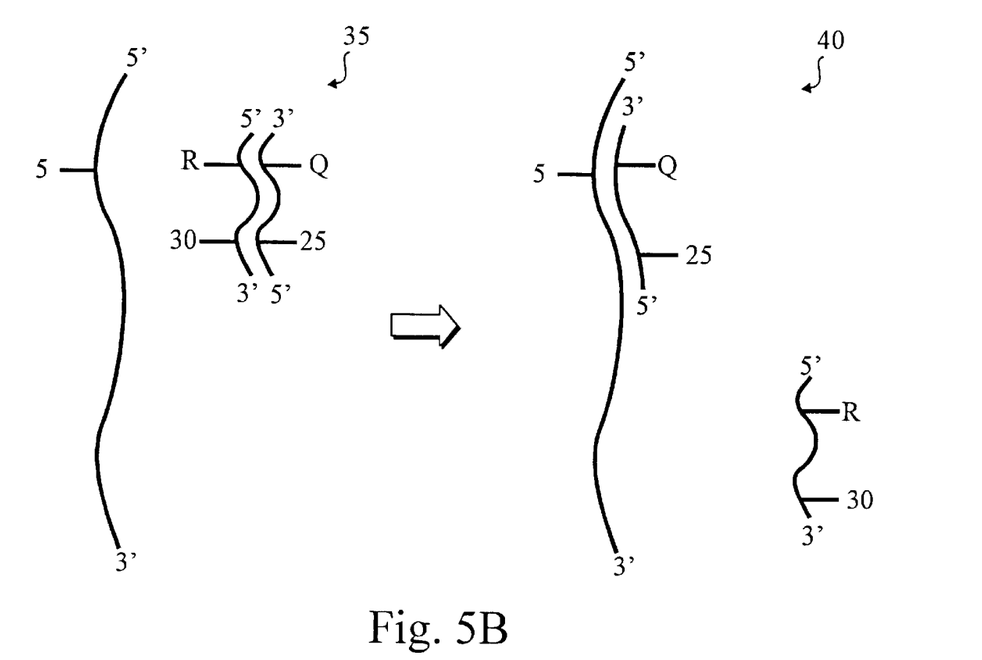

In a second assay format, shown in FIG. 5B, two oligonucleotide probes 25 and 30 which are complementary to each other and which each contain a reporter or a quencher label are used. The location of the labels is selected such that when the probes are hybridized to one another to form a probe-probe hybrid 35, the quenching interaction is favored, whereas an insignificant amount of quenching occurs when the probes are separated. The detection of target nucleic acid is achieved by denaturing both the target nucleic acid 5 and the probes 25 and 30, and then allowing the strands to reanneal. Thus, there is a competition between probe-probe hybridization and probe-target hybridization. The more target nucleic acid that is present, the larger the number of probes that will hybridize to the target forming probe-target hybrids 40. The presence of target DNA is indicated by an increased emission from the reporter R due to the reduced quenching by the quencher Q caused by a reduction in the number of probe-probe hybrids. (Morrison, European Patent Application 232 967 (1987)).

Figure 5C:
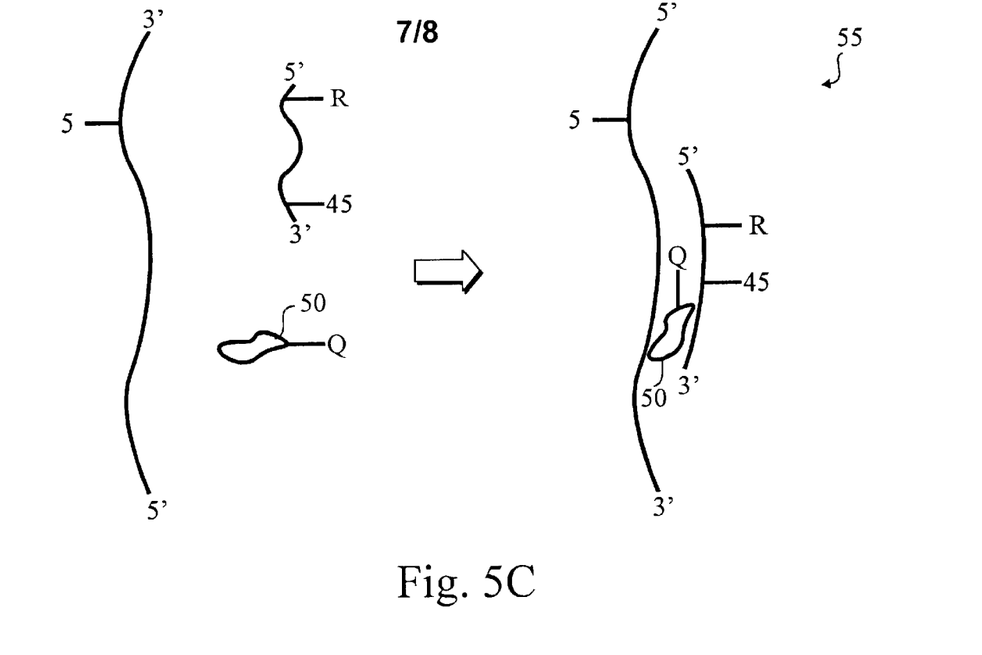

A third assay formnat, depicted in FIG. 5C, uses only one labelled probe 45 and a dye that binds preferentially to double-stranded nucleic acid 50. This dye 50 may intercalate between the base pairs of the double-stranded species or may bind to the outside of the helix and serves as a quencher. Thus, in the absence of hybridization, the quencher Q does not bind to the single-stranded probe 45, and the reporter R is unaffected by Q. However, in the presence of a target nucleic acid 5, the probe 45 hybridizes to the target nucleic acid and Q binds to the resulting double-stranded region forming a target-probe-dye complex 55. In the complex, Q and R are placed in close proximity and energy transfer or fluorescence quenching may take place. Thus, in this format, the emission of the reporter is quenched upon the hybridization of the probe to the target. (Heller and Morrison, In *Rapid Detection and Identification of Infectious Agents* (D. T. Kingsbury and S. Falkow, eds.), pp 245–256, Academic Press (1985)).

Figure 5D:
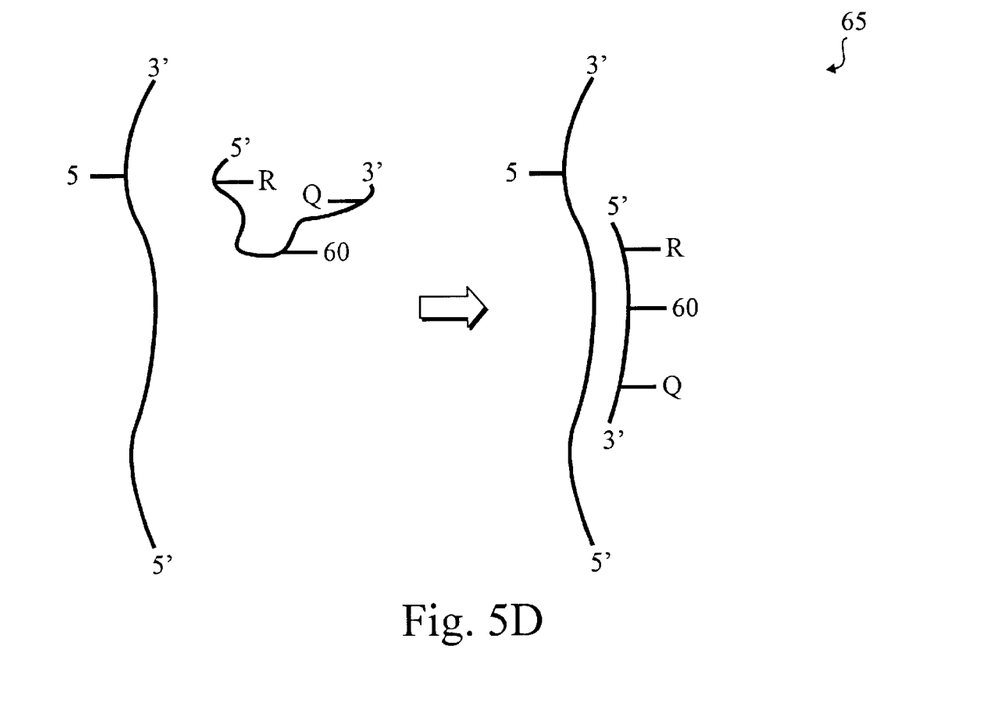

In a fourth assay format, shown in FIG. 5D, a single probe 60 is used which is labelled with both a reporter and a quencher. The location of the reporter and quencher labels is selected so that when the probe is in a single stranded state, i.e., unhybridized to a target nucleic acid, the single-stranded conformation of the probe is such that the reporter and quencher labels are in close proximity thereby allowing energy transfer to take place. In one alternative method of achieving this single-stranded confirmation, the reporter and quencher are brought into close proximity by designing the probe sequence such that a hairpin forms at the ends of the probe thereby forcing the reporter and quencher together (Bagwell, European patent Application No. 601 889 (1994); Tyagi and Kramer, *Nature Biotechnology*, 14: 303–308 (1996)). In another alternative method for achieving this single-stranded conformation, the reporter and quencher are located far enough apart on the probe such that the random-coil confirmation of the single-stranded probe serves to bring the quencher and reporter into sufficiently close proximity (Mayrand, U.S. Pat. No. 5,691,146). However, when the double-labelled probe 60 is hybridized to a target nucleic acid 5 forming a probe-target hybrid 65, the reporter and quencher are separated from one another, and the quenching interaction is prevented. Thus, in this format, the emission of the reporter becomes unquenched upon the hybridization of the probe to the target.

Figure 5E:
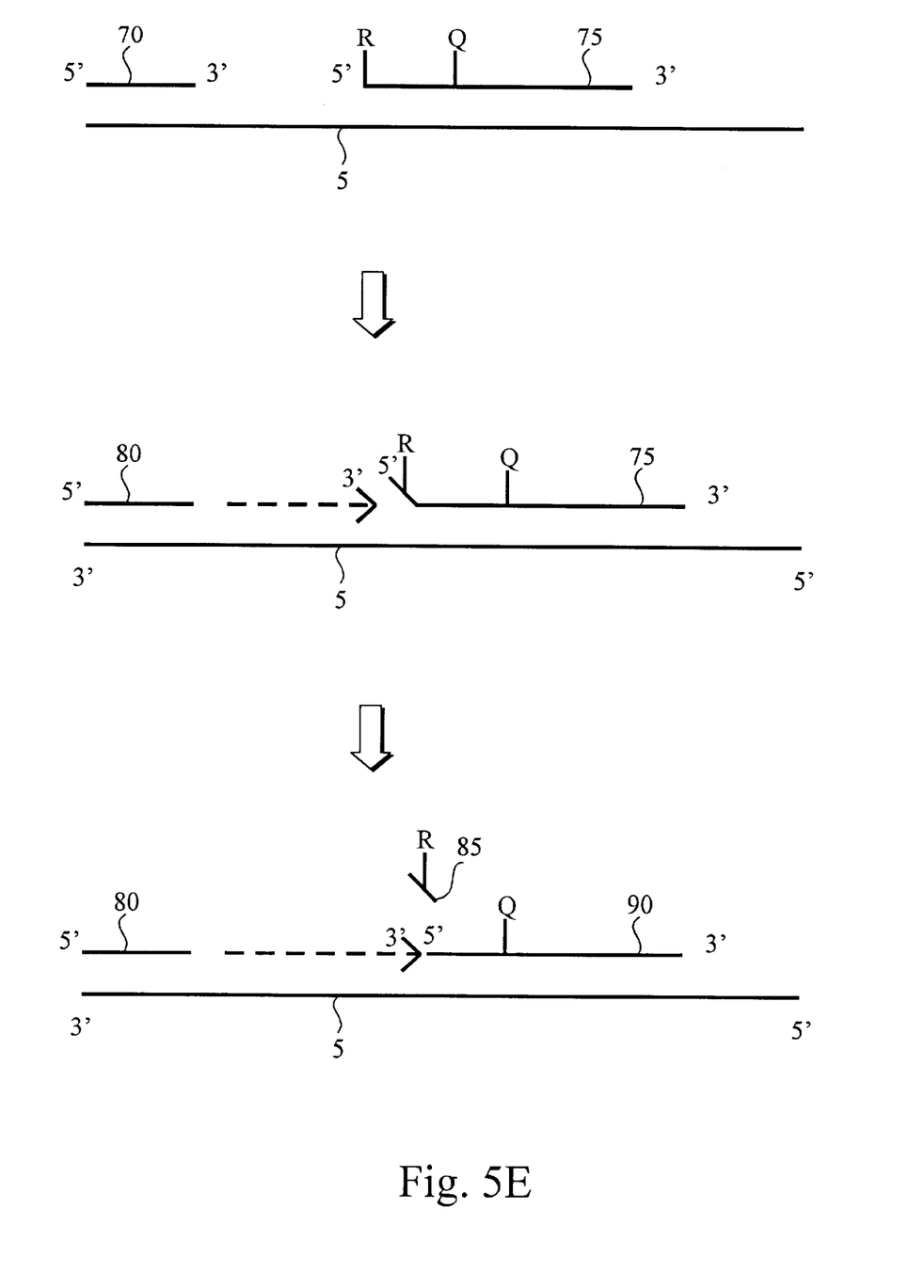

In a fifth assay format, referred to herein as the "Taqman" assay and illustrated in FIG. 5E, a doubly-labelled probe including both a reporter label and a quencher label is digested upon hybridization to a target nucleic acid thereby liberating one or both of the labels from the probe (Holland et al., *Proc. Natl. Acad. Sci. USA*, 88: 7276–7280 (1991); Livak, U.S. Pat. No. 5,538,848). In this method the doubly-labelled probe 75 is hybridized to a target nucleic acid 5. In addition, an oligonucleotide primer 70 is hybridized to the target nucleic acid at a position upstream from the probe, i.e., closer to the 3'-end of the target nucleic acid. The primer 70 is than extend using a polymerase enzyme thereby forming an extended primer 80, e.g., using a DNA polymerase. During the primer extension reaction, a 5'-3' nuclease activity of the polymerase serves to cut the probe 75 so as to form a first probe fragment 85 including the reporter label and a second probe fragment 90 including the quencher label. Thus, the reporter and quencher labels are separated thereby preventing energy transfer between the two. Thus, in this format, the emission of the reporter becomes unquenched upon the hybridization of the probe to the target and subsequent digestion of the probe.

Note that in each of the five assay formats discussed above and depicted in FIGS. 5A–E, unless otherwise specified, the location of the reporter and quencher is arbitrary. That is, while the reporter may be depicted on one probe and the quencher on another probe, their positions may be reversed.

While the assay formats described above are represented in terms of systems employing only a single reporter label, multi-reporter systems may also be practiced. Such multi-reporter systems are advantageous in applications requiring the analysis of multiple hybridization events in a single reaction volume. In such systems, each of the reporter molecules produce emissions which are spectrally resolvable from the emissions from any of the other reporters. The particular quencher used with each reporter can be the same or different, depending on the spectral properties of the quencher and reporter.

Each of the assays described above may be conducted in combination with a nucleic acid amplification step, e.g., PCR. That is, prior to conducting the hybridization assay, all or part of the nucleic acid sample may be amplified. When performed in combination with an amplification step, the hybridization assay may be conducted in an end-point mode or a real-time mode. In an end-point mode, the hybridization assay is performed after the amplification reaction is complete, e.g., after all or substantially all of the amplification cycles of a PCR reaction have been completed. In a real-time mode, a hybridization assay is performed multiple times during the amplification reaction, e.g., after each thermocycle of a PCR process (Higuchi, European Patent Application No. 512 334). The real-time mode is preferred when a quantitative measure of the initial amount of target nucleic acid is required, e.g., the copy-number of pathogen nucleic acid present in a blood sample.

V. EXAMPLES

The invention will be further clarified by a consideration of the following examples, which are intended to be purely exemplary of the invention and not to in any way limit its scope.

Example 1

Synthesis of Nitrothiazole Blue 5 and Nitrothiazole Orange 9

Figure 3A:
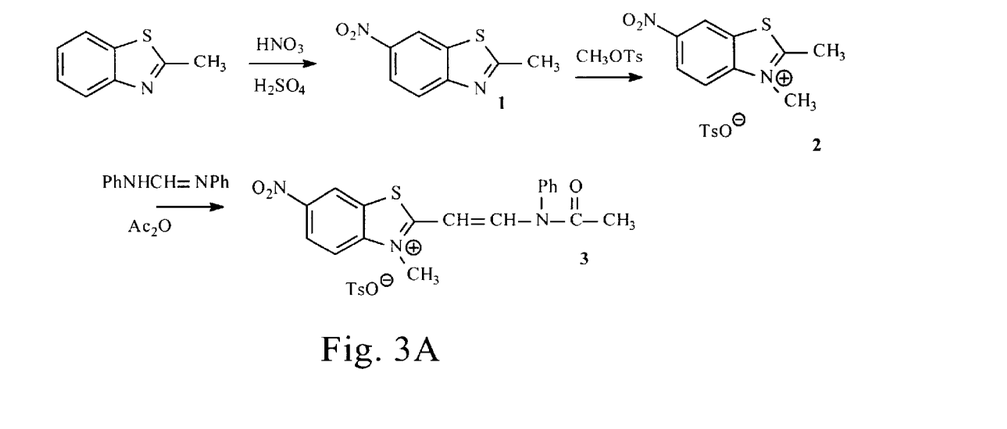
FIGS. 3A–3C show a synthetic scheme for the synthesis of a first preferred cyanine dye quencher of the present invention.
Figure 3B:
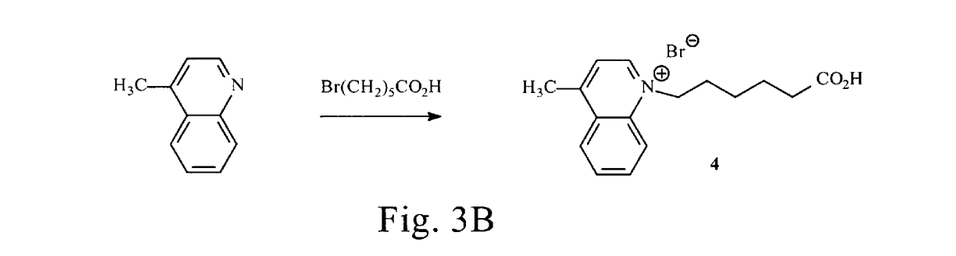
Figure 3C:
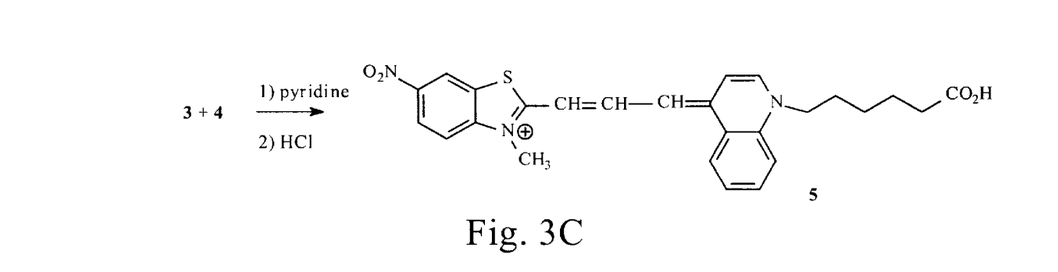
Figure 4A:
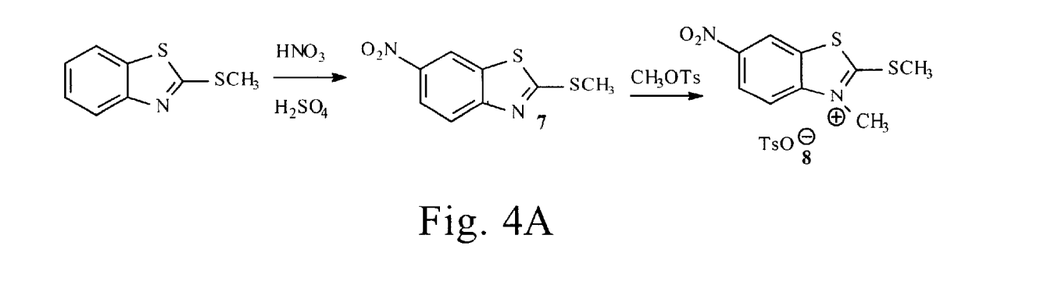
FIGS. 4A and 4B show a synthetic scheme for the synthesis of a second preferred cyanine dye quencher of the present invention.
Figure 4B:
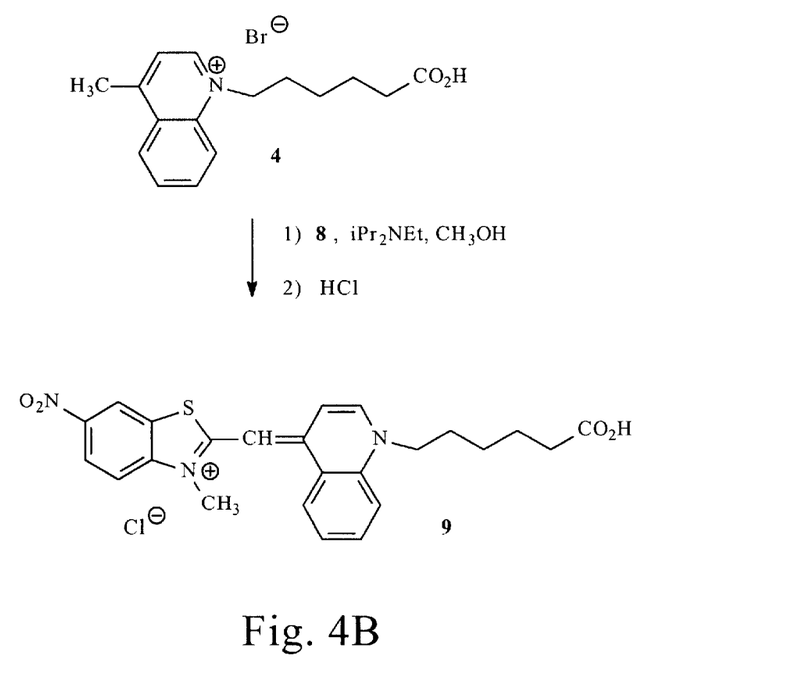

The syntheses of nitrothiazole blue 5 and nitrothiazole orange 9 are outlined in FIGS. 3 and 4.

Preparation of 6-Nitrobenzothiazole 1.

See FIG. 3A. Nitration of 2-methylbenzothizole was performed following the method of Mizuno, *J. Pharm. Soc. Japan*, 72, 745 (1952). A mixture of fuming nitric acid (1.6 mL) and concentrated sulfuric acid (1.2 mL) was added to an ice-cooled solution of 2-methylbenzothiazole (2 g) in sulfuric acid (8 mL). The solution was allowed to warm to room temperature for one hour, then poured onto 100 mL of ice. The solid was filtered, washed with water, and recrystallized from ethanol (80 mL) to provide 2.5 g of yellowish needles.

Preparation of 3-Methyl-6-nitrobenzothiazolium p-Toluenesulfonate 2.

See FIG. 3A. A mixture of 6-nitrobenzothiazole (1 g) and methyl-p-toluenesulfonate (1.2 g) was heated to 140° C. for 20 min. The solid was washed with acetone and filtered to provide a bluish solid (1.1 g).

Preparation of 2-(2'-Acetanilidovinyl)-3-methylbenzothiazolium p-Toluenesulfonate 3

See FIG. 3A. A mixture of 3-methyl-6-nitrobenzothiazolium p-toluenesulfonate 2 (200 mg, 0.52 mmol), diphenylfornamidine (160 mg, 0.8 mmol) and acetic anhydride (2 mL) was refluxed for 20 min. The cooled solution was triturated with ether to provide a dark brown solid (200 mg).

Preparation of 1-(5'-Carboxypentvly-lepidimium Bromide 4.

See FIG. 3B. A mixture of lepidine (5 g) and 6-bromohexanoic acid (10 g) was heated to 130° C. for 6 h. The solid was washed with acetone and filtered to provide an off-white solid (10.5 g).

Preparation of Nitrothiazole Blue 5.

See FIG. 3C. A mixture of the acetanilide 3 (65 mg, 0.13 mmol) and the lepidinium bromide 4 (66 mg, 0.2 mmol) and pyridine (1 mL) was combined and refluxed for 30 min. The blue solution was concentrated to dryness and washed with 5×1 mL 5% HCl. The residue was dried to provide a blue solid (67 mg).

Preparation of Nitrothiazole Blue Succinimidyl Ester.

To a solution of nitrothiazole blue 5 (31 mg, 0.056 mmol) in dimethylformamide (0.5 mL) and diisopropylethylamine (0.05 mL) was added O-(N-succimnmidyl)-N,N,N',N'-tetramethyluronium tetrafluoroborate (34 mg, 0.12 mmol). The mixture was warmed to 70° C. for 10 min. Reaction progress was monitored by TLC on silica gel using 600:60:16 dichloromethane:methanol:acetic acid as the eluant. To the homogeneous solution was added 5% HCl (2 mL). The precipitate was washed with additional HCl and dried to provide a dark solid (30 mg).

Preparation of 2-(Methylthio)-6-nitrobenzothiazole 7.

See FIG. 4A. Fuming nitric acid (1.93 g) was added dropwise to a solution of 2-(methylthio)benzothiazole (5 g) in concentrated sulfuric acid (16.8 g) cooled in an ice bath. After stirring at 5° C. for 3 h the solution was poured onto ice and filtered to provide a yellow solid (5.7 g, 25 mmol, 91%).

Preparation of 3-Methyl-2-(methylthio)-benzothiazolium p-Toluenesulfonate 8.

A mixture of 6-nitro-2-(methylthio)benzothiazole 7 (0.5 g, 2.2 mmol) and methyl-p-toluenesulfonate (3.7 g, 20 mmol) was heated from 120° C. to 145° C. over one hour. To the cooled solution was added 30 mL of ether. The resulting amorphous solid was triturated with acetone to provide a pale mauve solid (0.57 g, 1.4 mmol, 63%).

Preparation of Nitrothiazole Orange 9.

See FIG. 4B. To a solution of 3-methyl-2-(methylthio)-benzothiazolium p-toluenesulfonate 8 (50 mg, 0.12 mmol) and 1-(5'-carboxypentyl)-lepidinium bromide 4 (41 mg, 0.12 mmol) in methanol (5 mL) was added diisopropylethylamine (0.2 mL). The solution was refluxed for 15 min. The solvent was evaporated and the reaction residue triturated with 5% HCl (2 mL). The solid was washed with additional 5% HCl and dried to provide an orange solid (8 mg).

Preparation of Nitrothiazole Orange Succinimidyl Ester 10.

To a solution of nitrothiazole orange 9 (8 mg) in dimethylformamide (0.1 mL) and diisopropylethylamine (0.01 mL) was added O-(N-succinimidyl)-N,N,N',N'-tetramethyluronium tetrafluoroborate (10 mg). The mixture was warmed to 70° C. for 10 min. Reaction progress was monitored by TLC on silica gel using 600:60:16 dichloromethane:methanol:acetic acid as the eluant. To the homogeneous solution was added 5% HCl (1 mL). The precipitate was washed with additional HCl and dried to rovide an orange solid (8 mg).

Example 2

Preparation of Doubly-Labelled Probe for Taqman Assay

Automated synthesis of oligonucleotide probes was performed using an Applied Biosystems Model 394 DNA/RNA synthesizer (The Perkin-Elmer Corporation, PE Applied Biosystems Division (ABD)) according to the general procedures described in the operators manual. The oligonucleotides were synthesized in 0.2 μmol scale using dye-labelled CPG solid supports (Mullah and Andrus, *Tetrahedron Letters*, 38(33): 5751–5754 (1997)), DNA FastPhosphoramidites (User Bulletin number 85, 1994, ABD) and dye-labelled phosphoramidites, FAM and TET (User Bulletin number 78, 1994, ABD). The standard 0.2 μmol synthesis cycle was slightly modified by extending coupling time of FAM amidite by an additional 120 sec (User Bulletin number 78, 1994, ABD). Each probe included a reporter dye attached to a 5'-end of and a quencher dye located at a 3'-end of the probe.

After completion of the synthesis, oligonucleotides were autocleaved from the support on the DNA synthesizer by treating with a mixture of MeOH:t-BuNH$_2$:H$_2$O (1:1:2) (Woo et al., U.S. Pat. No. 5,231,191) using a 1 hr autocleavage procedure ("END CE" procedure) as described in the operators manual for the Applied Biosystems Model 394 DNA/RNA synthesizer. Base protecting groups were removed by heating the mixture at 85° C. for 1 hr or at 65° C. for 3 h.

The crude oligonucleotides were analyzed for purity and integrity by reverse phase HPLC using the following equipment and conditions: Perkin Elmer Series 200 solvent delivery system equipped with ABI 783A programmable detector; Perkin Elmer ISS200 autosampler; and PE Nelson 900 series data system; RP-18 reverse phase chromatography column (220×4.6 mm, ABD); solvent A: 0.1 M triethylammonium acetate; solvent B: CH$_3$CN; gradient 4–28% B in 35 min; flow rate: 1 mL/min; and detector: 260 nm.

Example 3

Taqman Assay for Human Beta Actin Gene

Human genomic DNA was prepared using conventional methods. The composition of the assay reagent was as follows (50 μl total volume):

| Component | Conc. | Volume (μl) |
| --- | --- | --- |
| dNTPs (dATP, dCTP, dGTP, dUTP) | 10 mM ea | 4 |
| MgCl2 | 25 mM | 7 |
| $^a$PCR Buffer, 10X | — | 5 |
| UNG | 1 unit/ml | 0.5 |
| Forward PCR Primer | 3 μM | 5 |
| Reverse PCR Primer | 3 μM | 5 |
| AmpliTaq ™ Gold DNA Polymerase | 5 units/ml | 0.25 |
| Human Male DNA | 10 ng/ml | 2 |
| Taqman Probe | 2 μM | 5 |
| Water | — | 16.3 |

$^a$10 mM KCl, 100 mM TRIS-HCl, 0.1 M EDTA, 600 nM passive internal standard, pH 8.3.

The reagents were combined in a 96-well microtiter tray and thermally cycled using the following protocol: 50° C. for 2 min; 95° C. for 10 min; 40 cycles of 95° C. for 15 sec followed by 60° C. for 1 min. Fluorescence was monitored during the amplification process using a Applied Biosystems Model 7700 Sequence Detection System (ABD).

The results of a taqman experiment can be analyzed using two parameters; the Rn value and the Ct value. The Rn value is the ratio of the fluorescence of a reporter dye and the fluorescence of a passive reference at the end of a PCR experiment. The Ct value, or threshold cycle number, is the PCR cycle number at which the fluorescence ratio is distinguishable from the background. For a given reporter dye and a fixed concentration of target, both the Rn and Ct values reflect the efficiency of the quencher.

The efficiency of NTB 5 was compared to that of TMR in quenching the reporters FAM and TET. The Rn and Ct values for NTB and TMR were indistinguishable for both reporter dyes. The quencher NTO 9 was used with FAM and found to be equivalent to both NTB and TMR. NTB was paired with the reporter, NED, to provide results that were similar to the other reporters. TMR could not be used as a quencher with the reporter dye NED because the fluorescence emissions of TMR and NED are at the same wavelength.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

We claim:

1. A labelled oligonucleotide comprising:

an oligonucleotide; and an asymmetric cyanine dye compound having the structure:

and including any associated counter ions, wherein:

n ranges from 0 to 2;

X is O, S or Se;

$R_1$ is selected from the group consisting of methyl and a linking group, or when taken together with the proximate carbon of the methine bridge forms a ring structure having from 5 to 7 members;

$R_2$ is a linking group;

$R_3$ is hydrogen, or when taken together with $R_4$ forms a fused aromatic bridge substituted with one or more nitro groups;

$R_4$ is hydrogen, or when taken together with either $R_3$ or $R_5$ forms a fused aromatic bridge substituted with one or more nitro groups;

$R_5$ is nitro, or when taken together with either $R_4$ or $R_6$ forms a fused aromatic bridge substituted with one or more nitro groups; and $R_6$ is hydrogen, or when taken together with either $R_5$ forms a fused aromatic bridge substituted with one or more nitro groups.

2. The labelled oligonucleotide of claim 1 in which $R_5$ is nitro and $R_3$, $R_4$ and $R_6$ are each hydrogen.

3. The labelled oligonucleotide of claim 1 in which $R_1$ or $R_2$ is lower alkylamine or lower alkylcarboxy.

4. The labelled oligonucleotide of claim 3 in which the lower alkylcarboxy is $-(CH_2)_q-N^+(CH_3)_2-(CH_2)_q-CO_2H$, where q ranges from 2 to 12.

5. The labelled oligonucleotide of claim 1 in which $R_1$ is methyl.

6. The labelled oligonucleotide of claim 1 in which X is sulfur.

7. The labelled oligonucleotide of claim 1 in which n is 0 or 1.

8. The labelled oligonucleotide of claim 1 in which $R_3$ and $R_4$ are each hydrogen and $R_5$ and $R_6$, taken together, are a fused aromatic ring substituted with one or more nitro groups.

9. The labelled oligonucleotide of claim 8 in which $R_5$ and $R_6$, taken together, are 3,5-dinitro(1,2)benzeno.

10. The labelled oligonucleotide of claim 1 in which $R_1$ is selected from the group consisting of methyl and a linking group.

11. The labelled oligonucleotide of claim 1 wherein the asymmetric cyanine dye has the structure:

12. The labelled oligonucleotide of claim 1 wherein the asymmetric cyanine dye has the structure:

13. The labelled oligonucleotide of claim 1 wherein the asymmetric cyanine dye has the structure:

14. The labelled oligonucleotide of claim 1 wherein the asymmetric cyanine dye has the structure:

15. The labelled oligonucleotide of claim 1 in which $R_1$ is taken together with the proximate carbon of the methine bridge and forms a ring structure having from 5 to 7 members.

16. The labelled oligonucleotide of claim 1 wherein the asymmetric cyanine dye has the structure:

17. The labelled oligonucleotide of claim 1 wherein the asymmetric cyanine dye has the structure:

18. The labelled oligonucleotide of claim 1 wherein the oligonucleotide comprises phosphate analogs selected from the group consisting of phosphorothioate, phosphorodithioate, phosphoroselenoate, phosphorodiselenoate, phosphoroanilothioate, phosphoranilidate, phosphoramiidate, and boronophosphates.

19. The labelled oligonucleotide of claim 1 wherein the oligonucleotide comprises base analogs selected from the group consisting of 2,6-diaminopurine, hypoxanthine, pseudouridine, C-5-propyne, isocytosine, isoguanline, and 2-thiopyfimidine.

20. The labelled oligonucleotide of claim 1 wherein the oligonucleotide comprises 2' or 3' modified sugar analogs selected from the group consisting of methoxy, ethoxy, allyloxy, isopropoxy, butoxy, isobutoxy, phenoxy, amino, alkylamino, fluoro, chloro, and bromo.

* * * * *

UNITED STATES PATENT AND TRADEMARK OFFICE
CERTIFICATE OF CORRECTION

PATENT NO.   : 6,541,618 B1                                                 Page 1 of 1
DATED        : April 1, 2003
INVENTOR(S)  : Linda G. Lee et al.

It is certified that error appears in the above-identified patent and that said Letters Patent is hereby corrected as shown below:

Column 4,
Line 32, delete "phosphorarnidate" and insert therefor -- phosphoramidate --

Column 7,
Lines 34-35, delete "positions 2 and and/or positions 3 and 4." and insert therefor -- positions 2 and 3; and/or positions 3 and 4. --

Column 18,
Line 42, delete "phosphoramiidate" and insert therefor -- phosphoramidate --
Line 47, delete "isoguanline" and insert therefor -- isoguanine --
Line 48, delete "2-thiopyfimidine" and insert therefor -- 2-thiopyrimidine --

Signed and Sealed this

Nineteenth Day of August, 2003

JAMES E. ROGAN
*Director of the United States Patent and Trademark Office*